United States Patent
Schmid

(10) Patent No.: US 6,538,031 B1
(45) Date of Patent: Mar. 25, 2003

(54) METHOD OF CONTROLLING SEA LICE INFESTATION IN FISH

(75) Inventor: Hariolf Schmid, Heitersheim (DE)

(73) Assignee: Novartis Animal Health US, Inc., Greensboro, NC (US)

( * ) Notice: Subject to any disclaimer, the term of this patent is extended or adjusted under 35 U.S.C. 154(b) by 0 days.

(21) Appl. No.: 09/718,120

(22) Filed: Nov. 20, 2000

(30) Foreign Application Priority Data

Nov. 25, 1999 (EP) .............................. 99811084

(51) Int. Cl.⁷ ................................ A01N 47/28
(52) U.S. Cl. ........................ 514/595; 514/596
(58) Field of Search ................. 514/595, 596

(56) References Cited

U.S. PATENT DOCUMENTS

| | | | |
|---|---|---|---|
| 4,857,510 A | 8/1989 | Knauf et al. | 514/30 |
| 4,897,486 A | 1/1990 | Böger | 514/300 |
| 5,153,224 A | 10/1992 | Drabek et al. | 574/594 |
| 5,420,163 A | 5/1995 | Potter et al. | 514/594 |
| 5,504,081 A | 4/1996 | Löhr et al. | 514/225 |

FOREIGN PATENT DOCUMENTS

| | | | |
|---|---|---|---|
| AU | 8176090 | * | 4/1982 |
| EP | 0 079 311 | | 5/1983 |
| EP | 0 179 021 | | 4/1986 |
| EP | 0 271 923 | | 6/1988 |
| EP | 0 590 425 A1 | | 4/1994 |
| WO | 92/08352 | | 5/1992 |
| WO | 96/25852 | | 8/1996 |
| WO | 96/41536 | | 12/1996 |
| WO | 97/21350 | | 6/1997 |
| WO | 98/25466 | | 6/1998 |
| WO | 99/27906 | | 6/1999 |
| WO | 99/44425 | | 9/1999 |
| WO | 99/63824 | | 12/1999 |
| ZA | 7802440 | * | 4/1979 |

OTHER PUBLICATIONS

Grayson T. H., et al., "Immunization of Atlantic salmon against the salmon louse: identification of antigens and effects on louse fecundity," Journal of Fish Biology, vol. 47 (Supplement A), pp. 85–94 (1995).

* cited by examiner

*Primary Examiner*—Kevin E. Weddington
(74) *Attorney, Agent, or Firm*—Michael U. Lee

(57) ABSTRACT

A method of successfully controlling sea lice in commercial fish farming, in an efficient and environmentally friendly way, with the compounds named in claim 1, preferably by injection, and a method of automating this type of control, are described.

8 Claims, No Drawings

METHOD OF CONTROLLING SEA LICE INFESTATION IN FISH

This application claims foreign priority benefit of European Patent Application No. 99811084.5 filed Nov. 25, 1999.

The present invention in the field of commercial fish farming for meat production relates to the control of parasites, which attach themselves to the skin of fish. To be more precise, it relates to the control thereof using the active substances named in claim 1, preferably by injection.

Fish farming, particularly when used to produce meat, operates nowadays on a large scale in so-called fish farms, where numerous fish are farmed in a confined area until they are ready for slaughter or for sale. As with any intensive livestock farming, in this case also, diseases and parasite infestation can lead to substantial losses and thus to drastic financial losses. As well as diseases caused by microorganisms such as Protozoa or by fungi, ecto-parasites that are customarily called sea lice, play a particularly decisive role.

Sea lice have absolutely nothing to do with insects, but as described in more detail below, belong to the fish-parasitic crustacea. There are in particular two members of the class of Copepodae [hoppers], which lead to substantial losses in yield, namely Lepeophtheirus [*Lepeophtheirus salmonis*] and Caligus [*Caligus elongatus*]. Primarily, they are popularly known as sea lice. They are easily recognised by their brown horseshoe-shaped shell, with Lepeophtheirus being considerably larger than Caligus.

These sea lice bite the fish firmly and damage it by eating the scales, the cell tissue and the mucous membrane. In the case of severe infestation, these parasites even penetrate into deeper layers of tissue. The immune system of the fish is weakened, leading to secondary infections and an excessive accumulation of water in the tissue. Frequently, the excessive parasite infestation leads to increasing tissue damage and, due to natural or artificial ultraviolet radiation or due to osmotic shock or the secondary infection, finally leads to death of the fish. Even with a light infestation, the fish lose body weight and only reach the right size for slaughter very slowly, if at all. In addition, infested fish have an unpleasant appearance and are not accepted by bulk buyers and end consumers.

By now, the sea louse can be found on almost all fish farms. Mortality rates based on infestation by sea lice of more than 50% have been reported by Norwegian fish farms. The extent of damage depends on the season and environmental influences, such as the salt content of the water and the average water temperature. In an initial phase, the sea louse infestation is observed by the parasites attached to the fish, and later on—more significantly—by the damage to the skin and the tissue. The greatest damage is observed on smolts which are in that period of life in which they migrate from fresh water to sea water. The whole situation is made worse by the specific conditions in the fish-breeding farms, where often salmon of different years, but the same class of weight, are kept together; soiled nets or cages are used; high salt concentrations are found; little running water flows through the nets and cages, and the fish are kept in a very small area.

Fish farmers who are confronted with these parasite problems have to accept substantial financial losses and additional costs. On the one hand, their fish are weakened and damaged by the lice, which leads to lower rates of weight increase; and on the other hand secondary infections have to be kept in check with expensive medicines and labour-intensive measures. In many cases, the goods can no longer be sold, as the damaged fish deter the consumers. For salmon breeders, this problem of lice infestation may threaten their existence.

The greatest damage is produced by Lepeophtheirus, since even a few parasites cause vast tissue damage. The life cycle of Lepeophtheirus consists basically of two larval stages living freely in water [Naupilus and Copepodia stages], four Chalimus stages, one pre-adult and the actual adult stage. The Chalimus and adult stages are host-dependent.

The most dangerous, since they produce the greatest damage, are all the fish-parasitic stages of sea louse, in particular the actual adult stages.

In the meantime, a series of chemical substances have been used against these sea lice with more or less success, e.g. trichlorfon [dimethyl-2,2,2-trichloro-1-hydroxyethyl-phosphonate], which requires concentrations of 300 ppm in salt water, and dichlorvos [2,2-dichloroethenyl-dimethylphosphate], which is effective from 1 ppm. A disadvantage of these preparations is the relatively high application rates, and the environmental contamination associated therewith, which also applies all the more because of the relatively high half-life periods. Other more selective substances that are used successfully are described e.g. in EP-497,343, EP-590,425, EP-781,095 and WO 97/21350. The fish are usually treated orally, e.g. through the food, or topically, i.e. externally by means of bath treatment, for example in a "medicinal bath" into which the fish are placed and kept for a period [minutes to several hours], e.g. transferring from one breeding tank to another. If there is no possibility of transferring the fish into a special tank, normally temporary or long-lasting treatment of the habitat of the fish takes place, e.g. in net cages, whole ponds, aquariums, tanks or basins, in which the fish are kept. In individual cases, treatment also takes place parenterally, e.g. by injection, especially if this is a hand-picked specimen for further breeding or ornamental fish as part of a hobby.

Although there are substances that show good efficacy against fish parasites, there is a need for further active substances that are more effective, can be tolerated by the underwater flora and fauna, or can be handled without problems by the breeder. Of course, the shelf life and stability in feed mixtures are also important. In addition, practicable application methods are desired, which save time and energy or further reduce environmental contamination. In this rapidly expanding industry, the above factors play an ever increasing role and can be crucial to commercial success.

WO 92/06599 describes the administration of oral compositions to fish and depicts this as an especially advantageous method compared with the labour-intensive and complex injection of individual fish. An injection is described as a particular stress factor, which at the very least leads to a temporary reduction in growth.

In contrast to this, it has now surprisingly been established that, with appropriate handling, the injection can have significant advantages over the other types of administration, if it is used in mass breeding using suitable apparative measures. It was established that the injection nowadays does not have to be restricted to specific cases, e.g. for especially expensive breeding and ornamental fish or for individually selected sick fish, but can be carried out with relatively little manual effort and using little time, even for whole schools of fish, without exposing the fish to exceptional stress. As will be shown in the following, whole schools of hundreds or thousands of fish may be treated in an almost stress-free manner, giving rise to quite significant advantages. The present invention accordingly relates also to the treatment of whole schools of fish, i.e. to commercial fish breeding for meat production, which is also known by the name "fish-farming". Under no circumstances should this be confused with the known occasional treatment of individual sick fish or with individual experiments to establish the efficacy of a potential active ingredient.

The conventional treatment processes that are successful per se of course also have their down side. The serious disadvantages of the current water treatment method are that the active substance and the remaining formulation excipients are not specifically targeted to the fish or the parasites, but extend inevitably over the whole habitat of the fish and may interact with the underwater flora and fauna or in detrimental cases may even reach the drinking water. Therefore, either extremely selective active substances must be used, or the fish must be transferred to closed basins or tanks for the duration of treatment and treated there whilst screened from the environment. However, the problem that remains after successful treatment is the removal of the water from the basin or tank. In addition, because it is inevitable that the active ingredient is diluted, a drastic excess dosage must be used for it to reach the parasites in a sufficiently active concentration. Fish food, in which the active ingredient has been incorporated, is fraught with the same problems.

Another great disadvantage of conventional treatment methods is that the active substance remains in the water over rather long periods of time in a greatly diluted and thus sub-lethal dose, which can substantially encourage resistance to build up in the target parasites.

On the other hand, if the active substance or a corresponding preparation is injected, the dose can be precisely coordinated to the body weight and substantially counteract the formation of resistance. In the case of fish being bred for meat production, this is especially easy to accomplish, as the whole population is of the same age and weight. Using the injection method, there is no overdosing or underdosing, and the environment remains as unharmed as possible, since it has no contact whatsoever with the active ingredient.

Of course, each fish could be treated by hand using an injection syringe. In fact, this would be time-and labour-intensive and certainly a venture associated with a certain amount of stress for the fish.

It has now however surprisingly been found that the above problem can be solved much more elegantly in commercial fish farming by treating a whole school of fish with an automatic or semi-automatic injection device. What is essential to this method is that the fish to be treated are guided in single file past an automatic inoculation device which administers the correct single dose to each fish, based on body weight and severity of infestation. In a preferred embodiment, this takes place by forcing the school of fish through a narrow passage, e.g. a narrow channel or trough, in which there is an addition constriction, for example a small elevation or another type of additional obstacle, so that the fish have to cross this narrow passage in single file and have to briefly stop at the said additional obstacle. If this channel is preferably kept so shallow that the dorsal area of the fish remains just below the surface of the water or even protrudes from the water a little, the fish is forced to navigate the narrow passage slowly. If the flow of fish is additionally checked or stopped by a further obstacle, each individual fish can be administered with the optimum dose within a short time, e.g. either by hand using an injection syringe or preferably with an appropriate injection device, e.g. an inoculating gun, thus making the procedure semi-automatic.

If necessary, one or more grids or other obstacles may be provided across the flow, to slow down the progress of the school in the narrow channel, so that no fish is overlooked or can pass through untreated. Using a mechanical, optical, thermal or movement sensor, treatment may be further automated, so that each fish that passes the sensor makes a contact, which brings the injection device into an appropriate position and carries out the injection. Through these measures, the actual proportion of manual work and the duration of the treatment procedure are reduced to a minimum and the stress for the animals to be treated is kept to an acceptable limit.

It has been demonstrated that the fish rapidly overcome the short shock phase and no longer show any stress reactions even one day after treatment. At latest two days later the fish show absolutely normal eating and group behaviour and their weight shows the usual increase. In addition, the targeted dosage which is spread evenly over the population ensures that the parasite infestation is reduced in a totally balanced manner over the entire population and sets in more quickly than in the case of water treatment. When treating the water, a balanced reduction is only attainable by means of massive overdosing.

This injection method can be used not only as a curative method, but also, advantageously, prophylactically. The latter is even preferable, as the vitality of the fish is maintained and there is no damage from the parasites that has to be cured. In addition, this type of prophylactic treatment is cheaper because of the low dosage, especially when compared with the water treatment method, and moreover is very environmentally friendly.

In the context of the present invention, injection is understood to mean not only all measures which are carried out using a needle, but also needleless methods, in which the active substance is fired through the skin using pressure, e.g. from an inoculation gun as used in human or animal medicine. The injection according to the invention provides administration through the skin, primarily into muscle or fat tissue.

The method according to the invention of controlling sea lice in commercial fish farming consists in applying an amount of an appropriate active substance that is effective against sea lice not through the medium water, but percutaneously and therefore directly to each member of a school of fish. Percutaneous is understood to mean preferably the above-mentioned types of injection.

The preferred embodiments of the present invention include, interalia:

A method of controlling sea lice in commercial fish farming, characterised in that an amount of an appropriate active substance that is effective against sea lice is administered individually to each fish either manually, semi-automatically or by an automated injection device, whereby semi-automatic and especially automatic administration are preferred.

A further important aspect of the present invention consists in the usage of an automated injection device for administering a dosage of a substance that is effective against sea lice, the dosage being effective per single fish, in a method of controlling sea lice on fish in commercial fish farming.

In accordance with the invention, the described method is used to advantage for the control of sea lice, which from a botanical aspect belong to the fish-parasitic crustacea. These include inter alia the Copepodae [hoppers] of the genera Ergasilus; Bromolochus; Chondracaushus; Caligus [*Caligus curtus, Caligus elongatus*]; Lepeophtheirus

[*Lepeophtheirus salmonis*]; Elythrophora; Dichelestinum; Lamproglenz; Hatschekia; Legosphilus; Symphodus; Ceudrolasus; Pseudocycmus; Lemaea; Lemaeocera; Pennella; Achthares; Basanistes; Salmincola; Brachiella; Epibrachiella; Pseudotracheliastes; and the familes: Ergasilidae; Bromolochidae; Chondracanthidae; Calijidae; Dichelestiidae; Philichthyidae; Pseudocycnidae; Lemaeidae; Lemaepotidae; Sphyriidae; Cecropidae, as well as the Branchiuriae [crabs] of the family Argulidae and the genera Argulus spp.; and the Cirripediae [barnacles] and *Ceratothoa gandichaugii*.

The targets of the treatment according to the invention are commercial fish of all ages, which live in freshwater, sea water and brackish water, e.g. carp, eel, trout, whitefish, salmon, bream, roach, rudd, chub, sole, plaice, halibut, Japanese yellowtail [*Seriola quinqueradiata*], freshwater eel [*Anguilla japonica*], red seabream [*Pagurus major*], sea bass [*Dicentrarchus labrax*], grey mullet [*Mugilus cephalus*], pompano, gilthread seabream [*Sparus auratus*], Tilapia spp., Cichlidae species such as Plagioscion, Channel catfish.

The treatment according to the invention is especially suitable for breeding salmon. The term salmon in the context of the present invention includes all members of the family of Salmonidae, especially those of the subfamily Salmonini and preferably the following species: *Salmon salar*[Atlantic salmon]; *Salmon trutta*[brown or sea trout]; *Salmon gairdneri*[rainbow trout]; as well as the Pacific salmon [Oncorhynchus]: *Oncorhynchus gorbuscha; Oncorhynchus keta; Oncorhynchus nekra; Oncorhynchus kisutch, Oncorhynchus tshawytscha* und *Oncorhynchus mason;* also included, however, are the species modified by breeding, e.g. Salvelinus species and *Salmo clarkii*.

Particularly preferred targets of the present invention are the Atlantic and Pacific salmon and the seawater trout.

In modern salmon and trout farming, young fish at the smolt stage are transferred from freshwater basins to seawater cages [salt water]. These are usually cubic, rectangular or even round cages consisting of a basic metal frame surrounded by a relatively fine-mesh net. These cages are lowered into the sea to ca. 9/10 and anchored, so that they are accessible from the top. The treatment process according to the invention can be employed particularly well using this transfer method. This prevents the active substance from being released into the sea and having an adverse affect on other sea creatures.

In another variant, the fish are kept in seawater basins or tanks of different forms. The cages are arranged in bays in the sea in such a way that the current constantly passes through and a sufficient oxygen supply is assured. The salt water in the seawater tanks is also kept in circulation with a supply of oxygen. In the artificial environment, the fish are fed until they are sufficiently matured and can be used commercially as food or can be sorted for further breeding. Here also, with single or multiple relocation, the injection process according to the invention can be used successfully.

In these fish breeding farms, there is extremely intensive cage maintenance. The density of fish reaches the order of 10 to 25 kg fish/m$^3$. With this monoculture and the extremely high fish concentrations, together with the usual stress factors, the fish caught are generally found to be considerably more susceptible to diseases, epidemics and parasites than the free-living members of the same species. For treatment against sea lice by the process according to the invention, the relocation method to other cages may be used, whereby the fish are shepherded through the initially-described narrow passage to the injection device.

The total dose of injection for the same active ingredient may vary from one species of fish to another and even within one species, since it depends inter alia on the weight, the age and the constitution of the fish. Furthermore, the dose depends on the activity of the active ingredient employed.

Advantageous doses are between 10 and 100 mg/kg body weight, preferably between 20 and 70 mg/kg body weight.

As injection preparations according to the invention, the active ingredients are normally not applied in pure form, but preferably in the form of a composition or preparation which contains, in addition to the active ingredient, application-enhancing constituents or formulation excipients, whereby such constituents are beneficial to the fish. In general, beneficial constituents are the formulation excipients for injection preparations which are physiologically tolerated by humans and animals and are known from pharmaceutical chemistry.

Such injection compositions or preparations to be used according to the invention usually contain 0.1 to 99% by weight, especially 0.1 to 95% by weight, of a substance that is active against sea lice, e.g. a compound of formula (I), and 99.9 to 1% by weight, especially 99.9 to 5% by weight, of a liquid, physiologically acceptable excipient, including 0 to 25% by weight, especially 0.1 to 25% by weight, or a non-toxic surfactant and water.

Whereas it is preferred to formulate commercial products as concentrated injection formulations, the end user will also use dilute formulations.

The formulations suitable for injection are for example aqueous solutions of the active ingredients in water-soluble form, e.g. a water-soluble salt, in the broader sense also suspensions of the active ingredients, such as appropriate oily injectable suspensions, whereby e.g. to delay the release of active ingredient (slow release), suitable lipophilic solvents or vehicles are used, such as oils, e.g. sesame oil, or synthetic fatty acid esters, e.g. ethyl oleate, or triglycerides, or aqueous injectable suspensions containing viscosity-increasing agents, e.g. sodium carboxymethyl cellulose, sorbitol and/or dextran, and where appropriate stabilisers. Oil-containing formulations with delayed release of active ingredient are called depot preparations here and hereinafter, and they belong to the preferred embodiments of the present invention, since, especially in the case of prophylactic administration, they are able to protect the fish for long periods from an infestation by the sea lice.

In the following examples, if not expressly stated to the contrary, the term "active ingredient" represents 1-[4-chloro-3-(3-chloro-5-trifluoromethyl-2-pyridyloxy)phenyl]-3-(2,6-difluoro-benzoyl)urea.

Formulation examples

Example A: Ampoule containing the active ingredient, disodium pamidronat pentahydrate and water. After dissolution concentration 3 mg/ml). the solution can be used for injections.

| Composition: | |
|---|---|
| active ingredient | 15.0 mg |
| mannitol | 250 mg |
| water for injection | 5 ml |

Example B: Injection solution for usage in an inoculation gun, containing 25 g active ingredient in 10 ampoules each containing 250 ml

| Composition: | |
|---|---|
| active ingredient | 25.0 g |
| sodium chloride | 22.5 g |
| phosphate buffer solution (pH: 7.4) | 300.0 g |
| demineralised water | ad 2.500.0 ml |

Example C: Injectables with delayed release of active ingredient

| Oily vehicles (slow release) | |
|---|---|
| active ingredient | 0.1–1.0 g |
| groundnut oil | ad 100 ml |
| or | |
| active ingredient | 0.1–1.0 g |
| sesame oil | ad 100 ml |

The active ingredient is dissolved in part of the oil whilst stirring and, if required, with gentle heating, then after cooling made up to the desired volume and sterile-filtered through a suitable membrane filter with a pore size of 0.22 μm.

The active ingredient and the sodium chloride are dissolved in 1000 ml of demineralised water and the solution filtered through a micro-filter. The filtrate is mixed with the phosphate buffer solution and the resulting mixture diluted with demineralised water to a volume of 2500 ml and filled into 25 ml ampoules, each containing 1000 mg of active ingredient.

Example D: Further injection formulations

| D1 Aqueous suspension | |
|---|---|
| active ingredient (micronised) | 1–5 g |
| povidone | 5 g |
| sodium chloride | 0.9 g |
| phosphate buffer solution | 10 g |
| benzyl alcohol | 2 g |
| water for injection | ad 100 ml |

| D2 Solubilisate | |
|---|---|
| active ingredient | 0.1–0.5 g |
| POE-660-hydroxystearate | 15 g |
| propylene glycol | 65 g |
| benzyl alcohol | 4 g |
| water for injection | ad 100 ml |

| D3 Oily suspension | |
|---|---|
| active ingredient (micronised) | 1–5 g |
| medium-chained triglycerides (Miglyol 812) | ad 100 ml |

In the process according to the invention, it is possible to use all known active substances that have proved beneficial in conventional processes for controlling sea lice. The process according to the invention is not restricted to a specific class of substance. Appropriate substances and classes of substance, including their preparation and sphere of activity, are described e.g. in the following printed specifications: EP-0,407,343; WO 97/21350; EP-0,590,425; EP-0,894,434; EP-0,781,094; and WO 92/06599.

A further important aspect of the present invention is based on the surprising knowledge that benzoylurea derivatives of formula (I) below are eminently suitable for controlling sea lice and may be used both in traditional processes and in the process of the invention.

The said benzoylurea derivatives are compounds of formula (I) which are known per se

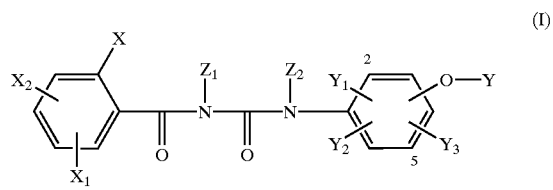

(I)

wherein

X is halogen, $X_1$ is hydrogen or halogen; $X_2$ is hydrogen or halogen; Y is partially or wholly halogenated $C_1$–$C_6$-alkyl; or partially or wholly halogenated $C_1$–$C_6$-alkyl interrupted by an oxygen atom; or partially or wholly halogenated $C_2$–$C_6$-alkenyl; or if —O—Y is in position 3, represents the group

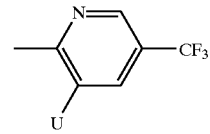

$Y_1$ is hydrogen or halogen; $Y_2$ is hydrogen or halogen; $Y_3$ is hydrogen or halogen; $Z_1$ is hydrogen or $C_1$–$C_3$-alkyl; $Z_2$ is hydrogen or $C_1$–$C_3$-alkyl; and U is hydrogen or halogen; with the exception of 1-[3,5-dichloro-4-(1,1,2,2-tetrafluoroethoxy)phenyl]-(2,6-difluorobenzoyl)-urea.

An especially preferred group of compounds of formula (I) is formed by those in which the radical —O—Y is in position 4 or especially position 3, and denotes

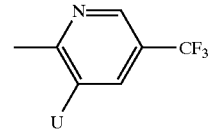

whereby U is hydrogen or in particular chlorine.

The alkyl groups present in the definitions of the substituents may be straight-chained or branched, depending on the number of carbon atoms, and they may be for example methyl, ethyl, propyl, butyl, pentyl or hexyl, as well as the branched isomers thereof, for example isopropyl, isobutyl, sec.-butyl, tert.-butyl, isopentyl, neopentyl or isohexyl. Typical radicals Y, which denote partially or completely halogenated $C_1$–$C_6$-alkyl, or partially or completely halogenated $C_1$–$C_6$-alkyl which is interrupted by one oxygen atom, or partially or completely halogenated $C_2$–$C_6$-alkenyl, are: straight-chained or branched $C_1$–$C_6$-alkyl radicals, which are partially or wholly substituted by identical or different halogen atoms and whose carbon chain is uninterrupted or is interrupted at one position by an oxygen atom, or straight-chained or branched $C_2$–$C_6$-alkenyl radicals with a carbon double bond, such as $OCF_3$, $OC_2F_5$, $OC_3F_7$, $OC_4F_9$, $OC_5F_{11}$, $OC_6F_{13}$, $OCF(CF_3)_2$, $OCF(C_2F_5)(CF_3)$, OCF $(C_2F_5)(C_2F_5)$, $OCF_2OCF_3$, $OCF_2OCF(C_2F_5)_2$, $OCF_2CHFCF_3$, $OCH(CF_3)CF_2CF_3$, $OCH(CF_3)CF_2F_5$, $OCF=CFCF_3$, $OCF_2CF_2=CFCF_3$, $OCF_2(CF_3)CF_2=CFCF_3$, $OCF_2(CF_3)-O-CF_2=CFCF_3$ $OCF_2CFHOCF_3$, $OCF_2CCl_3$, $OCF_2CHCl_2$, $OCF_2CHF_2$, $OCF_2CFCl_2$, $OCF_2CHBr_2$, $OCF_2CHClF$, $OCH_2CHBrCH_2Br$, $OCF_2CHBrF$, $OCClFCHClF$, etc. Alkoxy radicals are derived from the said alkyl groups. Halogen normally signifies fluorine, chlorine, bromine or iodine, preferably fluorine or chlorine, especially chlorine, whereby a partially or completely halogenated substituent may contain one or more identical or different halogen atoms. Whilst giving due consideration to the number of carbon atoms contained from case to case in the corresponding group, alkenyl is either straight-chained, for example vinyl, 1-methylvinyl, allyl, 1-butenyl or 2-hexenyl, or branched, for example isopropenyl.

A number of benzoylureas, which come under formula (I), and also their preparation and usage, are described in U.S. Pat. No. 5.420.163 and in the literature cited therein.

Compounds of formula (I), wherein —O—Y is in position 4; X is F; $X_1$ is 6-F; $X_2$ is H; Y is $CF_2CHFCF_3$; $Y_1$ is 2-F; $Y_2$ is 3-Cl; $Y_3$ is 5-Cl; $Z_1$ is H, methyl or ethyl; and $Z_2$ is H, methyl or ethyl, and wherein at least $Z_1$ or $Z_2$ is methyl or ethyl, are described in WO 98/19542.

Compounds of formula (I), wherein —O—Y is in position 4; X is F; $X_1$ is 6-F; $X_2$ is H; Y is $CF_2CHFCF_3$; $Y_1$ is 3-Cl, $Y_2$ is H; $Y_3$ is 5-Cl; $Z_1$ is H, methyl or ethyl; and $Z_2$ is H, methyl or ethyl, and wherein at least $Z_1$ or $Z_2$ is methyl or ethyl, are described in WO 98/19543.

Compounds of formula (I), wherein —O—Y is in position 4; X is F; $X_1$ is 6-F; $X_2$ is H; Y is $CH(CH_3)CF_2R$; R is $CF_3$ or $CF_2CF_3$; $Y_1$ is 2-H or F; $Y_2$ is 3-Cl; $Y_3$ is 5-Cl; $Z_1$ is H; and $Z_2$ is H, are described in WO 98/19995.

Compounds of formula (I), wherein —O—Y is in position 4; X is F; $X_1$ is 6-F; $X_2$ is H; Y is $CF=CFCF_3$ or $CF_2CF_2=CFCF_3$; $Y_1$ is 3-Cl; $Y_2$ is H; $Y_3$ is 5-Cl; $Z_1$ is H; and $Z_2$ is H, are described in WO 98/19994.

A benzoylurea derivative of formula (I), wherein —O—Y is in position 4, X is F, $X_1$ is 6-F; $X_2$ is H; Y is $CF_2CFHOCF_3$; $Y_1$ is 3-Cl; $Y_2$ is H, $Y_3$ is H; $Z_1$ is H; and $Z_2$ is H; is described in WO 98/25466.

One known representative of formula (I) is lufenuron from EP-0.179.021. The substance in question here is (R,S)-1-[2,5-dichloro-4-(1,1,2,2,3,3,3-hexafluoropropoxy)-phenyl]-3-(2,6-difluorobenzoyl)urea.

Another known representative of formula (I) is novaluron from EP-0.271.923. The substance in question here is (±)-1-[3-chloro-4-(1,1,2,trifluoro-2-trifluormethoxyethoxy)-phenyl]-3-(2,6-difluorobenzoyl)urea.

Another known representative of formula (I) is fluazuron from EP-0.079.311. The substance in question here is 1-[4-chloro-3-(3-chloro-5-trifluoromethyl-2-pyridyloxy)phenyl]-3-(2,6-difluorobenzoyl)urea. Further representatives of this type of structure, as well as their preparation as insecticides and acaricides, are described in this publication.

Another representative is known from U.S. Pat. No. 4.857.510. This is chlorfluazuron. 1[3,5dichloro-4-(3-3-chloro-5-trifluoromethyl-2-pyridyloxy)phenyl]-3-(2,6-difluorobenzoyl)urea. Further representatives of this type of structure, as well as their preparation as insecticides and acaricides, are described in this publication.

The following publications also clarify the technological background of the present invention: Grayson T. H. et al., "Immunization of Atlantic salmon against the salmon louse: identification of antigens and effects on louse fecundity", Journal of Fish Biology, vol. 47, Suppl. A, 1995, pages 85–94: describes the immunisation of Atlantic salmon by injection of extracts of Lepeophtheiris salmonis. WO 96/41536 describes the use of teflubenzuron in the control of parasites, which infest the fish in fish farms. WO 92/08352 relates to the control of fish parasites by using avermectins and milbemycins. WO 97/21350 describes the usage of a group of oxadiazine derivatives against fish parasites. EP-0.590.425 describes the control of fish parasites with agonists and antagonists of the nicotinergenic acetylcholine receptors of insects. WO 98/25466 describes the usage of novaluron against parasites such as mites, ticks, lice, fleas, beetles, helminths and protozoa on warm-blooded animals, such as humans, cattle, horses, sheep, goats, poultry, pigs, cats and dogs. U.S. Pat. No. 5.420.163 describes the systemic administration of benzoylureas to warm-blooded animals to control various parasites. There is no reference to the treatment of fish either in WO 98/25466 or in U.S. Pat. No. 5.420.163. WO 99/27906 relates to injection formulations based on castor oil, which have long-term efficacy. Lufenuron is also included in the proposed active ingredients. There is no mention of fish in WO 99/27906. WO 99/44424 describes the use of lufenuron and closely related derivatives for the control of fungal diseases. WO 96/25852 relates to mixtures of two classes of active ingredient against ecto- and endo-parasites on domestic animals and productive livestock, but not on fish. One consists of certain benzoylureas and the other is a milbemycin, avermectin, milbemycin oxime, moxidectin, ivermectin or abamectin. EP-0.271.923 relates to the insecticidal activity of N-(2,6-difluorobenzoyl)-N'-3-chloro-4-[1,1,2-trifluoro-2-(trifluoromethoxy)ethoxyphenyl-ureas. U.S. Pat. No. 4.857.510 describes the usage of combinations of macrocyclic lactones, such as abamectin and certain benzoylureas, primarily against insects and their stages of development in crop protection, forestry, material protection and in hygiene; fish are not mentioned. EP-0.179.021 relates to compositions for controlling insects and acarids, which contain certain benzoylureas as active ingredients. EP-0.079.311 describes other benzoylureas for the control of animal- and plant-parasitic ectoparasites. The treatment of fish against fish parasites is not mentioned in EP-0.179.021 or EP-0.079.311. A few of the publications mentioned refer to the theoretical possibility of perhaps administering the active substance to fish via injection, but neither disclose nor indicate an injection process that is suitable for usage in large-scale breeding for meat production.

WO 99/63824 subsequently published on 16.12.1999 describes the use of hexaflumuron (1-[3,5-dichloro-4-(1,1,2,2-tetrafluoroethoxy)phenyl]-(2,6-difluorobenzoyl)urea) against fish parasites. As well as oral administration, the injection of hexaflumuron is also described.

To illustrate the present invention, the following typical and preferred representatives of compounds of formula (I) are listed in the following tables. These are known from the publications mentioned above, or may be prepared analogously to the known representatives.

TABLE 1

Preferred benzoylureas of formula (I) with —O—Y in position 4

| No. | X | $X_1$ | $X_2$ | $Z_1$ | $Z_2$ | Y | $Y_1$ | $Y_2$ | $Y_3$ |
|---|---|---|---|---|---|---|---|---|---|
| 1.01 | F | 6-F | H | H | H | $CF_2CHFCF_3$ | 2-Cl | 5-Cl | H |
| 1.02 | F | 6-F | H | H | H | $CF_2CHFCF_3$ | 2-F | 3-Cl | 5-Cl |
| 1.03 | F | 6-F | H | H | $CH_3$ | $CF_2CHFCF_3$ | 2-F | 3-Cl | 5-Cl |
| 1.04 | F | 6-F | H | H | $C_2H_5$ | $CF_2CHFCF_3$ | 2-F | 3-Cl | 5-Cl |
| 1.05 | F | 6-F | H | $CH_3$ | H | $CF_2CHFCF_3$ | 2-F | 3-Cl | 5-Cl |
| 1.06 | F | 6-F | H | $CH_3$ | $CH_3$ | $CF_2CHFCF_3$ | 2-F | 3-Cl | 5-Cl |
| 1.07 | F | 6-F | H | $CH_3$ | $C_2H_5$ | $CF_2CHFCF_3$ | 2-F | 3-Cl | 5-Cl |
| 1.08 | F | 6-F | H | $C_2H_5$ | H | $CF_2CHFCF_3$ | 2-F | 3-Cl | 5-Cl |
| 1.09 | F | 6-F | H | $C_2H_5$ | $CH_3$ | $CF_2CHFCF_3$ | 2-F | 3-Cl | 5-Cl |
| 1.10 | F | 6-F | H | $C_2H_5$ | $C_2H_5$ | $CF_2CHFCF_3$ | 2-F | 3-Cl | 5-Cl |
| 1.11 | F | 6-F | H | H | H | $CF_2CHFCF_3$ | 3-Cl | H | 5-Cl |
| 1.12 | F | 6-F | H | H | $CH_3$ | $CF_2CHFCF_3$ | 3-Cl | H | 5-Cl |
| 1.13 | F | 6-F | H | H | $C_2H_5$ | $CF_2CHFCF_3$ | 3-Cl | H | 5-Cl |
| 1.14 | F | 6-F | H | $CH_3$ | H | $CF_2CHFCF_3$ | 3-Cl | H | 5-Cl |
| 1.15 | F | 6-F | H | $CH_3$ | $CH_3$ | $CF_2CHFCF_3$ | 3-Cl | H | 5-Cl |
| 1.16 | F | 6-F | H | $CH_3$ | $C_2H_5$ | $CF_2CHFCF_3$ | 3-Cl | H | 5-Cl |
| 1.17 | F | 6-F | H | $C_2H_5$ | H | $CF_2CHFCF_3$ | 3-Cl | H | 5-Cl |
| 1.18 | F | 6-F | H | $C_2H_5$ | $CH_3$ | $CF_2CHFCF_3$ | 3-Cl | H | 5-Cl |
| 1.19 | F | 6-F | H | $C_2H_5$ | $C_2H_5$ | $CF_2CHFCF_3$ | 3-Cl | H | 5-Cl |
| 1.20 | F | 6-F | H | H | H | $CH(CH_3)C_2F_5$ | 3-Cl | H | 5-Cl |
| 1.21 | F | 6-F | H | H | H | $CH(CH_3)C_2F_5$ | 3-Cl | 2-F | 5-Cl |
| 1.22 | F | 6-F | H | H | H | $CH(CH_3)C_2F_4CF_3$ | 3-Cl | H | 5-Cl |
| 1.23 | F | 6-F | H | H | H | $CH(CH_3)C_2F_4CF_3$ | 3-Cl | 2-F | 5-Cl |
| 1.24 | F | 6-F | H | H | H | $CF=CFCF_3$ | 3-Cl | H | 5-Cl |
| 1.25 | F | 6-F | H | H | H | $CF_2CF_2=CFCF_3$ | 3-Cl | H | 5-Cl |
| 1.26 | F | 6-F | H | H | H | $CF_2CFHOCF_3$ | 3-Cl | H | H |
| 1.27 | F | 6-F | H | H | H | $CF_2CFHOCF_3$ | 2-Cl | H | H |
| 1.28 | F | 6-F | H | H | H | $CF_3$ | 2-Cl | 5-Cl | H |
| 1.29 | F | 6-F | H | H | H | $CF_2CHClF$ | 2-Cl | 5-Cl | H |
| 1.30 | F | 6-F | H | H | H | $CF_2CHCHCl_2$ | 2-Cl | 5-Cl | H |
| 1.31 | F | 6-F | H | H | H | $CF_2CHCFBr$ | 2-Cl | 5-Cl | H |
| 1.32 | F | H | H | H | H | $CF_2CHFCF_3$ | 2-Cl | 5-Cl | H |
| 1.33 | Cl | H | H | H | H | $CF_2CHFCF_3$ | 2-Cl | 5-Cl | H |
| 1.34 | F | 6-Cl | H | H | H | $CF_2CHFCF_3$ | 2-Cl | 5-Cl | H |
| 1.35 | F | 6-F | H | H | H | 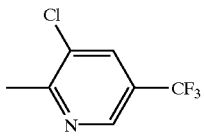 | 3-Cl | 5-Cl | H |

TABLE 2

Preferred benzoylureas of formula (I) with —O—Y in position 3, whereby Y is

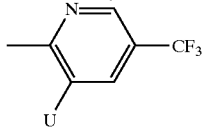

and Y2 is in position 4:

| No. | X | $X_1$ | $X_2$ | $Z_1$ | $Z_2$ | U | $Y_1$ | $Y_2$ | $Y_3$ |
|---|---|---|---|---|---|---|---|---|---|
| 2.01 | F | 6-F | H | H | H | Cl | H | $CH_3$ | H |
| 2.02 | F | 6-F | H | H | H | H | H | H | H |
| 2.03 | Cl | H | H | H | H | H | H | H | H |
| 2.04 | F | 6-F | H | H | H | CL | H | Br | H |
| 2.05 | Cl | 6-Cl | H | H | H | Cl | H | Br | H |
| 2.06 | Cl | H | H | H | H | Cl | H | Br | H |
| 2.07 | Cl | H | H | H | H | Cl | H | $CH_3$ | H |
| 2.08 | H | H | H | H | H | Cl | H | $CH_3$ | H |
| 2.09 | F | 6-F | H | H | H | H | H | Br | H |
| 2.10 | $CH_3$ | H | H | H | H | H | H | $CH_3$ | H |
| 2.11 | Br | H | H | H | H | Cl | H | $CH_3$ | H |
| 2.12 | $CH_3$ | H | H | H | H | Cl | H | $CH_3$ | H |
| 2.13 | Cl | H | H | H | H | Cl | H | $CH_3$ | H |
| 2.14 | Br | 6-Br | H | H | H | Cl | H | $CH_3$ | H |
| 2.15 | F | 6-F | H | H | H | H | H | $CH_3$ | H |
| 2.16 | F | 6-F | H | H | H | Cl | H | F | H |
| 2.17 | F | 6-F | H | H | H | Cl | H | Cl | H |
| 2.18 | F | 6-F | H | H | H | H | H | F | H |
| 2.19 | F | 6-F | H | H | H | H | H | Cl | H |

Biological Examples (Active Ingredient=Fluazuron)

1. In vivo Preliminary Test for Activity Against the Salmon Louse Following Manual Injection 20 naturally infected Atlantic salmon of various sizes from a fish farm are transferred to a well-aerated seawater aquarium for acclimatisation. They are left there for 3 days and fed daily with the usual food. On the fourth day, they are caught individually with a fish basket and quickly weighed.

Each fish is injected by hand using an injection needle with a single dose, according to formulation example 1, of 40 mg fluazuron/kg body weight into the muscle tissue below the dorsal fin. The treated fish are returned to their aquarium. 24, 48 and 72 hours later, the parasite infestation is inspected and the number of surviving parasites determined; it is shown that, at the dosage indicated, at latest after 72 hours all the adult and pre-adult stages have been killed.

2. Semi-automated in Vivo Test for Activity Against the Salmon Louse.

Two well-aerated seawater aquariums, each of 5000 liter content, are set up parallel to one another at a distance of 2 m, with one being 10 cm higher than the other. The upper aquarium is provided with a kind of overflow which opens into a plexiglass channel which is open at the top and has a square inner cross-section of 10 cm. The upper end of this channel is secured by a movable grid and rests on the edge of the lower aquarium. Between the two aquariums, there is slight gradient. In the middle of the channel, two wire grids are attached with a 30 cm gap across the current, in such a way that they are either used as a water-permeable barrier or can be opened upwards on a hinge by a lever. At the bottom of the upper aquarium, there is an electrically controlled tail lift. When this is raised, the volume of water above it is diminished by reducing the depth of water. In addition, the upper aquarium contains a water feed which is secured by a grid and the lower aquarium has outlet holes. Water flows constantly from the upper to the lower aquarium. 200 Atlantic salmon of the same age are introduced into the upper aquarium and are each artificially infected with 5 pre-adult, 5 adult female and 5 adult male salmon lice. The infected salmon are kept in the upper aquarium for 3 days in order to acclimatise and are fed regularly. On the fourth day, the grid blocking the channel is removed and the tail lift is slowly raised. Owing to the constantly diminishing depth of water on one side, the salmon head for the overflow and reach the connecting channel in single file. So that they do not reach the lower aquarium unchecked, the lower crosswise grid in the channel is closed, so that the salmon arriving first is stopped. Behind it, the second grid is likewise closed. Now, within seconds, a dose of 45 mg of fluazuron/kg body weight is given to the first salmon below the dorsal fin by setting up and activating a needleless inoculation gun. The lower grid is raised so that the salmon can swim on and is closed again behind it. Then, the upper grid is raised, the next salmon passes through and the upper grid is closed behind it immediately. Now, the second salmon is located between the two grids and is treated as the preceding one. The procedure is exactly the same with the remaining salmon until they have all been treated and are in the lower aquarium. After a further 24 hours, the parasite infestation is inspected and the number of surviving parasites determined; as in the preliminary test, it is shown that at the dosage indicated all the female and male adults and pre-adult stages have been killed.

What is claimed is:

1. A method of controlling sea lice infestation in fish comprising administering to fish or a habitat of fish an effective amount of a compound of formula (I)

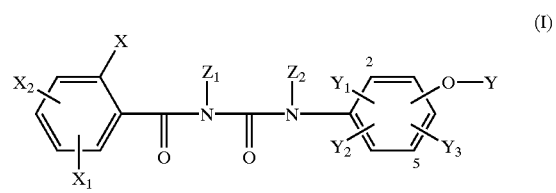

or of one of its physiologically tolerable acid addition salts, wherein X is halogen; $X_1$ is hydrogen or halogen; $X_2$ is hydrogen or halogen; Y is partially or wholly halogenated $C_1$–$C_6$-alkyl; or partially or wholly halogenated $C_1$–$C_6$-alkyl interrupted by an oxygen atom; or partially or wholly halogenated $C_2$–$C_6$-alkenyl; or if —O—Y is in position 3, represents the group

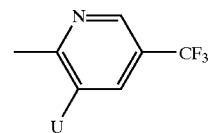

$Y_1$ is hydrogen or halogen; $Y_2$ is hydrogen or halogen; $Y_3$ is hydrogen or halogen; $Z_1$ is hydrogen or $C_1$–$C_3$-alkyl; $Z_2$ is hydrogen or $C_1$–$C_3$-alkyl; and U is hydrogen or halogen; with the exception of 1-[3,5-dichloro-4-(1,1,2,2-tetrafluoroethoxy)phenyl]-(2,6-difluorobenzoyl)urea.

2. The method according to claim 1, wherein the compound is selected from the group consisting of 1-[4-chloro-3-(3-chloro-5-trifluoromethyl-2-pyridyloxy)phenyl]-3-(2,6-difluorobenzoyl)urea; 1[3,5-dichloro-4-(3-3-chloro-5-trifluoromethyl-2-pyridyloxy)phenyl]-3-(2,6-difluorobenzoyl)urea; (±)-1-[3-chloro-4-(1,1,2,trifluoro-2-trifluoromethoxyethoxy)-phenyl]-3-(2,6-difluorobenzoyl)urea; and (R,S)-1-[2,5-dichloro-4-(1,1,2,2,3,3,3-hexafluoropropoxy)-phenyl]-3-(2,6-difluorobenzoyl)urea.

3. The method according to claim 1 wherein the administering is injecting a dosage of 10 to 100 mg/kg body weight.

4. The method according to claim 1 wherein the administering is by an injection device.

5. The method according to claim 4 wherein the fish are urged through a narrow passage in substantially single file and are caused to stop wherein each fish is administered an effective dose of-the compound of formula (I) according to claim 1.

6. The method according to claim 5 wherein the stop is caused by at least one grid across a flow of water.

7. The method according to claim 6 wherein the stop is controlled by a mechanical, optical, thermal or movement sensor, so that each fish that passes the sensor causes a signal, which brings the injection device into an appropriate position, and carries out the injection, and after the injection has taken place the stop is removed.

8. The method according to claim 1 wherein the injection device is an automatic inoculation device.

* * * * *